United States Patent [19]

Gregory

[11] Patent Number: 4,593,135

[45] Date of Patent: Jun. 3, 1986

[54] METHOD FOR PROMOTING THE ACTIVITY AND/OR EXTENDING THE LIFE OF CATION-EXCHANGEABLE LAYERED CLAY CATALYSTS IN PROTON-CATALYZED REACTIONS

[75] Inventor: Reginald Gregory, Camberley, England

[73] Assignee: The British Petroleum Company P.L.C., London, England

[21] Appl. No.: 577,314

[22] Filed: Feb. 6, 1984

Related U.S. Application Data

[62] Division of Ser. No. 408,036, Aug. 13, 1982, abandoned.

[30] Foreign Application Priority Data

Aug. 21, 1981 [GB] United Kingdom ................. 8125547

[51] Int. Cl.$^4$ .................. C07C 2/66; C07C 41/03; C07C 41/05; C07C 67/04; C07C 67/26
[52] U.S. Cl. ......................................... 585/446; 502/22; 502/64; 502/78; 502/80; 502/85; 502/514; 560/190; 560/200; 560/204; 560/209; 560/246; 560/247; 568/605; 568/697; 568/618; 568/619; 568/620; 585/710
[58] Field of Search ............... 560/204, 247, 190, 200, 560/209, 246; 568/605, 697, 618, 619, 620; 585/710, 446; 502/22, 64, 78, 80, 85, 514

[56] References Cited

U.S. PATENT DOCUMENTS

| | | | |
|---|---|---|---|
| 2,678,332 | 5/1954 | Cottle | 560/204 X |
| 3,037,052 | 5/1962 | Bortnick | 560/204 X |
| 3,096,365 | 7/1963 | Heisler et al. | 560/204 X |
| 4,440,958 | 4/1984 | Gregory et al. | 560/247 |

OTHER PUBLICATIONS

Grim, R. E. *Applied Clay Minerology*, McGraw-Hill Book Co., Inc., New York, pp. 310–320, (1962).

*Primary Examiner*—Natalie Trousof
*Assistant Examiner*—Vera C. Clarke
*Attorney, Agent, or Firm*—Brooks Haidt Haffner & Delahunty

[57] ABSTRACT

A method for promoting the activity and/or extending the life of a cation-exchangeable layered clay catalyst in reactions susceptible to catalysis by protons which method comprises the addition to the catalyst of water as the sole additive. The quantity of water employed is suitably up to 40%, preferably up to 10% based on weight of reactants. The layered clay catalyst can be for example montmorillonite, bentonite or vermiculite. Suitable proton catalyzed reactions include formation of esters, (e.g. by reaction of olefin and carboxylic acid), ethers, aldehydes, thioethers and alkylation and cracking reactions.

15 Claims, No Drawings

METHOD FOR PROMOTING THE ACTIVITY AND/OR EXTENDING THE LIFE OF CATION-EXCHANGEABLE LAYERED CLAY CATALYSTS IN PROTON-CATALYZED REACTIONS

This application is a division of application Ser. No. 408,036, filed Aug. 13, 1982, now abandoned.

The present invention relates to a method for promoting the activity and/or extending the life of cation-exchangeable layered clay catalysts in proton catalysed reactions.

Natural and synthetic clays having a lamellar structure with interlamellar spaces disposed between the lamellar layers are well known. Smectites, such as bentonite, montmorillonites and chlorites are a class of clays possessing such a lamellar structure. Montmorillonite has an idealised stoichiometric composition corresponding to $Na_{0.67}Al_{3.33}Mg_{0.67}Si_8O_{20}(OH)_4$. Structurally montmorillonite comprises a central octahedral co-ordination layer containing aluminium and magnesium oxides and hydroxides sandwiched between two tetrahedral co-ordination layers containing silicon oxide. These three layers are tightly bound together and form a single lamellar layer. Normally in nature $Na^+$ or $Ca^{2+}$ ions are present to compensate for the charge imbalance caused by isomorphous substitution of $Mg^{2+}$ or other ions for $Al^{3+}$ in the octahedral layer, and/or $Al^{3+}$ or other ions for $Si^{4+}$ in the tetrahedral layers. The space between the lamellar layers, ie the interlamellar space, in the naturally occurring clays is normally occupied by exchangeable $Ca^{2+}$ or $Na^+$ ions. The distance between the interlamellar layers can be increased substantially by absorption of various polar molecules such as water, ethylene glycol, amines, etc, which enter the interlamellar space and in doing so push the layers apart. The interlamellar spaces tend to collapse when the molecules occupying the space are removed by, for example, heating the clays at high temperature.

In the Journal of Catalysis 58, 238–252 (1979) Adams et al have disclosed that cation exchangeable water-intercalated clays such as water-intercalated montmorillonites in which the exchangeable ions are certain metal cations are catalysts for the conversion of alkenes to the corresponding bis-sec-alkyl ethers. Under the conditions described in this paper the reactants would be present in the liquid phase.

Our European patent publication Nos. 0031252 and 0031687 describe the use of cation-exchangeable layered clays in proton-catalysed reactions, eg esterification.

Furthermore our European application publication No. 45618 (BP Case No 5010) describes a method for promoting the activity of a cation-exchangeble layered clay or crystalline aluminosilicate catalyst in esterification, hydration, etherification and cracking reactions which method comprises the addition of a strong acid. In a particular embodiment of the method the life of a layered clay catalyst is extended by the addition of a strong acid together with water.

Although the addition of acid and water increases the life of a cation-exchangeable layered clay catalyst in reactions susceptible to catalysis by protons, we have now unexpectedly found that the addition of water alone can not only increase the life but can also increase the activity of layered clay catalysts in reactions of this type.

The present invention therefore provides a method for promoting the activity and/or extending the life of a cation-exchangeable layered clay catalyst in reactions susceptible to catalysis by protons which method comprises the addition to the catalyst of water as the sole additive.

With regard to the catalyst, the cation exchangeable layered clay may be selected from those normally classified as smectites or vermiculites. Examples of suitable layered clay minerals include montmorillonites, bentonites, hectorites, beidellites, vermiculites, nontronite and Fullers earths.

As mentioned hereinbefore the clays in their natural state normally contain exchangeable sodium or calcium ions in the interlamellar space. Such clays generally have some catalytic activity but generally it is preferred to exchange some or all of the exchangeable ions with other cations in order to increase their catalytic activity. Ion-exchange is a tecnique well known in the art. It is essential that there be used an ion-exchange method which avoids the use of excessively high temperatures which destroy the lamellar structure of the clay. Although any of the variants of that technique may be used in the preparation of catalysts useful in the process of the present invention, the cation-exchanged layered clay is preferably prepared by exchanging the sodium or calcium or other exchangeable cations normally associated with a natural clay with an aqueous solution of either an acid or a metal salt. Exchange is preferably effected at or near ambient temperature, though elevated temperatures which do not destroy the layered structure and the catalytic activity, eg up to about 35° C., may be employed. The period of contact will depend to some extend on the temperature. Typically, at ambient temperature the contact period may be in the range from ½ hour to 3 days, preferably about 2 days. For preparing the hydrogen ion-exchanged layered clay the acid may be a mineral acid, eg sulphuric acid and hydrochloric acid, or a carboxylic acid, preferably a mineral acid. The acid may suitably be from 0.5 to 10 molar. For preparing the metal cation-exchanged clay any suitable soluble metal salt, eg the sulphate, may be employed. Techniques for separating the cation-exchanged clay from the ion-exchange media and excess ions are also well known. Any suitable solid/liquid separation procedure followed by repeated resuspension of the solid in distilled water to remove excess cations and reseparation can be used. Decantation or centrifugation are two preferred methods for solid/liquid separation. After exchange, it is preferred to wash the exchanged clay until all extraneous cations are removed. Thereafter, the clay is preferably dried. Although drying is preferably effected at elevated temperature, temperatures which cause collapse of the lamellar structure should be avoided. Generally drying temperatures up to 200° C. are suitable and temperatures below 150° C. are preferred. The nature of the cation exchanged on to the clay may depend on the type of reaction which the cation-exchanged clay is to catalyse. Generally the preferred cations are hydrogen and aluminum. Other suitable cations include chromium, cobalt, nickel, iron, copper, vanadium, ammonium, magnesium and calcium ions.

The method of the invention is applicable to many types of reaction susceptible to catalysis by protons, including the following:

(i)

(a) the formation of esters by the reaction of an alcohol with a carboxylic acid. The conditions under which this reaction is carried out are well known in the art.

(b) the formation of esters by the reaction of an olefin with a carboxylic acid. With regard to the olefin reactant any olefin may be employed. Suitable olefins include ethylene, propylene, butenes, pentenes and hexenes and diolefins such as butadiene. Mixtures of olefins may also be used if so desired. Both aromatic and aliphatic carboxylic acids may be used. Suitable aliphatic acids include formic, acetic, propionic and butyric acids. Of the aromatic acids benzoic acid and phthalic acids, especially ortho-phthalic acid, may be employed. Preferably the olefin is ethylene, the carboxylic acid is acetic acid and the ester produced is ethyl acetate.

(c) the formation of esters by reacting one or more epoxides with one or more carboxylic acids. Reaction conditions which may be used are substantially the same as those employed for the reaction of an olefin with a carboxylic acid.

(ii)
(a) the formation of ethers by the reaction of an alcohol with an olefin. Suitable alcohols include methanol, ethanol, propanols, butanols, pentanols and hexanols, of which linear alcohols are preferred. Diols, polyols and aryl alcohols may also be employed. With regard to the olefin any suitable olefin may be employed. Suitable olefins include ethylene, propylene, butenes, pentenes hexenes, and diolefins such as butadiene and cyclic olefins such as cyclohexene. Preferably the olefin is a $C_3$ to $C_6$ linear or branched olefin. Mixtures of olefins, including those commonly encountered in petroleum refinery streams such as those obtained by steam cracking of hydrocarbons may also be used if so desired. Preferably the alcohol is methanol, the olefin is isobutene and the ether produced is methyl tertiary butyl ether.

(b) the formation of ethers by reacting one or more epoxides with one or more alcohols, polyols or polysaccharides. With regard to the epoxide reactant, ethylene oxide and propylene oxide are preferred and with regard to the other reactant, methanol, ethanol, propanol, glycerol and cellulose are preferred. The reaction may be carried out at room temperature or at elevated temperatures, preferably at a temperature in the range 20° to 150° C., and under pressure if so desired.

(c) the formation of bis-sec-alkyl ethers by reaction of a primary or secondary aliphatic alcohol or polyol. With regard to the primary aliphatic alcohol reactant, suitable alcohols include $C_1$ to $C_8$ alkan-1-ols. As regards the secondary aliphatic alcohol, suitable alcohols include straight-chain alcohols, such as $C_3$ to $C_6$ alkan-2-ols, and cyclohexanol. Suitable polyols include alkylene glycols such as ethylene glycol and diethylene glycol. Mixtures of alcohols and/or polyols may also be used if so desired. The reaction may be carried out at a temperature in the range 100° to 300° C., preferably from 150° to 225° C. and at atmospheric or elevated pressures.

(d) the production of ethers by reacting one or more epoxides.

(iii) the cracking of hydrocarbons. The reaction is sufficiently well known that it requires no further elaboration as to suitable feeds and reaction conditions.

(iv) the formation of alpha, beta-unsaturated aldehydes by reacting aldehydes over cation-exchangeable layered clays.

(v) the production of a secondary or a tertiary amine by reacting at elevated temperature a primary or a secondary amine having a methylene group adjacent to an amino group, reaction of a primary amine resulting in the formation of a secondary amine and reaction of a secondary amine resulting in the formation of a tertiary amine.

(vi) the production of polyphenylenemethylene by reacting benzyl alcohol.

(vii) the production of thioethers by reacting alkanthiols at elevated temperature.

(viii) the production of alkyl aromatic compounds by reacting an aromatic hydrocarbon with an olefin or a $C_2$ or higher alcohol. The aromatic hydrocarbon may suitably be benzene, naphthalene or other polycyclic aromatic hydrocarbon. Aromatic hydrocarbons substituted by alkyl or other functional groups, such as for example, hydroxyl, alkoxy and hydroxyalkyl, may also be employed. Preferably the aromatic hydrocarbon is benzene or toluene. Mixtures of aromatic hydrocarbons may also be employed if so desired. The olefin may suitably be a mono-olefin or a diolefin. Suitable mono-olefins include ethylene, propylene and butylenes, though higher olefins, such as for example propylene tetramer, may be employed. Mixtures of olefins may also be employed. A suitable diolefin is butadiene. Examples of suitable $C_2$ or higher alcohols which may be employed include ethanol and propanol. In a preferred embodiment benzene is reacted with propylene to produce isopropylbenzene (cumene). In another preferred embodiment benzene is reacted with ethylene to produce ethylbenzene. Reaction of the aromatic hydrocarbon with the olefin or alcohol may suitably be effected in the liquid phase or the vapour phase, preferably in the liquid phase. Typically, the reaction may be carried out in the liquid phase at a temperature up to 300° C., preferably in the range 175° to 250° C. and at an elevated pressure sufficient to maintain the reactants in the liquid phase. In the vapour phase higher temperatures are generally employed. The process may be operated batchwise or continuously, preferably continuously.

The reactions (i)(b), (ii)(a) and (v) susceptible to catalysis by protons referred to above and the reaction conditions which may be used are described in detail in one or other of our European patent publication Nos. 0031687 and 0031252 which are incorporated herein by reference.

In carrying out the reactions according to the invention, water may suitably be added in an amount up to 40% by weight, preferably up to 10% by weight, based on the total weight of the reactants. Provided that the water is present during the reaction it may be added to the clay prior to addition of the reactants or it may be added with the reactants, or both.

Although the reactants may be carried out batchwise they are preferably operated in a continuous manner.

The invention will now be illustrated by reference to the following Examples and Comparative Tests. In the Examples and Comparative Tests reference will be made to hydrogen ion-exchanged Wyoming bentonite and aluminium ion-exchanged Wyoming and Texas bentonites. These were prepared as follows:

Hydrogen Ion-Exchanged Wyoming and Texas Bentonites

Wyoming bentonite was immersed in a dilute aqueous solution of sulphuric acid (5M) and left for 4 hours at room temperature. The clay was then washed to remove all extraneous ions and dried at 80° C. to give hydrogen-exchanged Wyoming bentonite.

Hydrogen-exchanged Texas bentonite was made in a similar manner but substituting Texas bentonite for Wyoming bentonite.

Aluminum Ion-Exchanged Wyoming and Texas bentonites

Wyoming bentonite was left in a solution of 0.5M aluminium chloride solution for 4 hours at room temperature. The clay was then washed to remove all extraneous ions and dried at 80° C. to give aluminium-exchanged Wyoming bentonite.

Aluminium ion-exchanged Texas bentonite was made in a similar manner but substituting Texas bentonite for Wyoming bentonite.

EXAMPLE 1

A reactor was charged with 20 ml of the hydrogen-exchanged Wyoming bentonite prepared in the manner hereinbefore described in the form of 200–280 mm mesh particle size mixed with 20 ml inert ⅛ inch cylinder packing to facilitate a better liquid flow path through the catalyst bed. Glacial acetic acid to which was added 2.5% by weight water was pumped through the catalyst bed at a rate of 40 ml/hour, providing an LHSV of 2 (calculated on active catalyst). The reactor was maintained at 40–50 bar ethylene pressure with a constant slow flow of ethylene over the catalyst.

A particular start-up sequence was used so as not to deactivate the catalyst prior to reaction. Acetic acid to which was added 2.5% by weight water was fed into the reactor to saturate the catalyst bed at a temperature of ca. 100° to 120° C. after which ethylene was allowed into the reactor and the system allowed to reach working pressure. The temperature was only then raised to a working value of 200° C. which was reached within 2 hours of start-up.

An initial catalyst activity of 50% conversion of acetic acid to ethyl acetate was achieved. The selectivity to ethyl acetate from acetic acid was 99%. A little ethanol was detected in the product, leading to a slight loss in the selectivity to ethyl acetate from ethylene. The catalyst activity declined slowly, the catalyst half-life being 75 hours.

EXAMPLE 2

As Example 1 but using 10 ml of the hydrogen ion-exchanged Wyoming bentonite and 10 ml inert packing with a 20 ml/hour feed of acetic acid containing 5% by weight of water.

An initial catalyst activity of 45% conversion of acetic acid to ethyl acetate was achieved. The selectivity to ethyl acetate from acetic acid was 99%. A little ethanol was also produced leading to a slight loss in the selectivity to ethyl acetate from ethylene. The catalyst activity declined slowly giving a catalyst half-life of about 135 hours.

EXAMPLE 3

As Example 2 but substituting aluminium ion-exchanged Texas bentonite for hydrogen ion-exchanged Wyoming bentonite. An initial catalyst activity of 48% conversion of acetic acid to ethyl acetate was achieved with a selectivity to ethyl acetate from acetic acid of 99%. Again some ethanol was produced. The catalyst half-life was 58 hours.

COMPARISON TEXT 1

The procedure of Example 1 was repeated except that no water was added to the acetic acid.

The initial activity of the catalyst under the reaction conditions was 30% conversion of the acetic acid to ethyl acetate. The conversion gradually declined and the catalyst half-life was estimated to be about 18 hours.

COMPARISON TEXT 2

As Comparison Test 1, except that aluminium ion-exchanged Wyoming bentonite was used instead of hydrogen-exchanged Wyoming bentonite. A similar initial catalyst activity of 28% conversion of acetic acid to ethyl acetate was achieved with a selectivity to ethyl acetate from acetic acid of 99%. The catalyst half-life was about 18 hours.

From these results it can be seen that the addition of water alone to the reactants not only increase the life of the catalyst but also increases its initial activity.

I claim:

1. A method for carrying out a reaction susceptible to catalysis by protons which method comprises contacting the reactants in the presence of a cation-exchangeable layered clay selected from the group consisting of smectites and vermiculites catalyst to which water is added as the sole additive thereby promoting or extending the activity of the catalyst.

2. A method according to claim 1 wherein water is added in an amount up to 40% by weight, based on the total weight of reactants.

3. A method according to claim 2 wherein water is added in an amount up to 10% by weight.

4. A method according to claims 1, 2 or 3 wherein the clay is a hydrogen ion-exchanged layered clay.

5. A method according to any one of claims 1 to 3 wherein the clay is an aluminium ion-exchanged layered clay.

6. A method according to claims 1, 2, or 3 wherein the reaction susceptible to catalysis by protons is the formation of esters by the reaction of an olefin with a carboxylic acid.

7. A method according to any one of claims 1 to 3 wherein the reaction susceptible to catalysis by protons is the formation of esters by the reaction of an epoxide with a carboxylic acid.

8. A process according to any one of claims 1 to 3 wherein the reaction susceptible to catalysis by protons is the formation of ethers by the reaction of an alcohol with an olefin.

9. A method according to any one of claims 1 to 3 wherein the reaction susceptible to catalysis by protons is the formation of ethers by the reaction of an alcohol with an epoxide.

10. A process according to any one of claims 1 to 3 wherein the reaction susceptible to catalysis by protons is the formation of bis-sec-alkyl ethers from a primary or secondary aliphatic alcohol or polyol.

11. A process according to any one of claims 1 to 3 wherein the reaction susceptible to cataysis by protons is the production of an alkyl aromatic compound by reacting an aromatic hydrocarbon either with an olefin or a $C_2$ or higher alcohol.

12. A process according to claim 11 wherein the aromatic hydrocarbon is benzene and the olefin is either propylene or ethylene.

13. A process according to any one of claims 1 to 3 wherein the reaction susceptible to catalysis by protons is the production of ethers from epoxides.

14. A method for carrying out a reaction susceptible to catalysis by protons which method comprises contacting the reactants with a cation-exchangeable layered clay selected from the group consisting of smectites and vermiculites catalyst to which water is added as the sole additive thereby promoting or extending the activity of the catalyst,
wherein the water is added to the clay catalyst before the reactants are contacted with the clay catalyst.

15. A method for carrying out a reaction susceptible to catalysis by protons which method comprises adding the reactants to a cation-exchangeable layered clay selected from the group consisting of smectites and vermiculites catalyst to which water is added as the sole additive thereby promoting or extending the activity of the catalyst,
wherein the water is added to the clay catalyst with the added reactants.

* * * * *